United States Patent
Gotte (10) Patent No.: US 9,852,268 B2
(45) Date of Patent: Dec. 26, 2017

(54) METHOD FOR DETERMINING CONTACT POSITION PARAMETERS OF A JOINT CONNECTING TWO BONES

(75) Inventor: Hubert Gotte, Munich (DE)

(73) Assignee: Brainlab AG, Munich (DE)

( * ) Notice: Subject to any disclaimer, the term of this patent is extended or adjusted under 35 U.S.C. 154(b) by 871 days.

(21) Appl. No.: 14/363,040

(22) PCT Filed: Dec. 9, 2011

(86) PCT No.: PCT/EP2011/072323
§ 371 (c)(1),
(2), (4) Date: Jun. 5, 2014

(87) PCT Pub. No.: WO2013/083201
PCT Pub. Date: Jun. 13, 2013

(65) Prior Publication Data
US 2014/0303947 A1   Oct. 9, 2014

(51) Int. Cl.
G06F 17/50   (2006.01)
G06F 19/00   (2011.01)
A61B 34/10   (2016.01)

(52) U.S. Cl.
CPC .......... *G06F 19/3437* (2013.01); *A61B 34/10* (2016.02)

(58) Field of Classification Search
USPC ........................... 703/2, 5; 345/473; 600/587
See application file for complete search history.

(56) References Cited

U.S. PATENT DOCUMENTS

| | | | |
|---|---|---|---|
| 6,708,142 B1* | 3/2004 | Baillot | G06T 17/00 345/473 |
| 7,699,793 B2* | 4/2010 | Gotte | A61B 5/1114 600/587 |
| 8,958,885 B2 | 2/2015 | Panken et al. | |
| 2002/0087274 A1 | 7/2002 | Alexander et al. | |
| 2005/0251065 A1 | 11/2005 | Henning et al. | |
| 2007/0179626 A1 | 8/2007 | de la Barrera et al. | |
| 2008/0269596 A1 | 10/2008 | Revie et al. | |
| 2009/0157083 A1 | 6/2009 | Park et al. | |

(Continued)

FOREIGN PATENT DOCUMENTS

| | | |
|---|---|---|
| DE | 102006056399 A | 5/2007 |
| WO | 2009076296 A2 | 6/2009 |
| WO | 20091076296 | 6/2009 |

OTHER PUBLICATIONS

International Search Report and Written Opinion for International Application No. PCT/EP2011/072323 dated Sep. 4, 2012.

(Continued)

*Primary Examiner* — Thai Phan
(74) *Attorney, Agent, or Firm* — Tucker Ellis LLP

(57) ABSTRACT

A data processing method for determining six parameters of a contact position of a joint which connects two bones, comprising the steps of acquiring a plurality of sample contact position datasets, each dataset comprising six parameters, acquiring a subset of n of the parameters of the contact position as an input parameter dataset, selecting at least two of the sample contact position datasets based on the input parameter dataset and determining the m=6−n remaining parameters of the contact position based on the at least two selected sample contact position datasets.

15 Claims, 6 Drawing Sheets

(56) References Cited

U.S. PATENT DOCUMENTS

| | | |
|---|---|---|
| 2009/0209884 A1 | 8/2009 | Van Vorhis et al. |
| 2009/0264894 A1 | 10/2009 | Wasielewski |
| 2010/0010380 A1 | 1/2010 | Panken et al. |
| 2011/0029116 A1 | 2/2011 | Jordan et al. |
| 2014/0303947 A1 | 10/2014 | Goette |
| 2014/0324061 A1 | 10/2014 | Gotte |
| 2014/0324403 A1 | 10/2014 | Gotte |
| 2015/0148653 A1 | 5/2015 | Fleig et al. |
| 2015/0294510 A1 | 10/2015 | Gotte et al. |

OTHER PUBLICATIONS

Van Der Esch et al: "Knee varus-valgus motion during gait—a measure of joint stability in patients with osteoarthritis?", Osteoarthritis and Cartilage, Bailliere Tindall, London, GB, vol. 16, No. 4, Mar. 29, 2008, pp. 522-525, ISSN: 1063-4584.

Walde T A et al, "Optimized functional femoral rotation in navigated total knee arthroplasty considering ligament tension", The Knee, Elsevier, Amsterdam, NL, vol. 17, No. 6, doi:10.1016/J.KNEE.2009.12.001, ISSN 0968-0160, pp. 381-386.

Blankevoort L et al, "The envelope of passive knee joint motion", Journal of Biomechanics, Pergamon Press, New York, NY, US, vol. 21, No. 9, ISSN 0021-9290, pp. 705-720.

Blankevoort L et al, "Articular contact in a three-dimensional model of the knee", Journal of Biomechanics, Pergamon Press, New York, NY, US, vol. 24, No. 11, doi:10.1016/0021-9290(91)90019-J, ISSN 0021-9290,pp. 1019-1031.

https://en.wikipedia.org/wiki/Norm_(mathematics) retrieved Aug. 2, 2017, pp. 1-11.

https://en.wikipedia.org/wiki/Spline_interpolation, retrieved Aug. 2, 2017, pp. 1-5.

\* cited by examiner

```
14  ml=-5 ap=-10 pd=30.2001 vv=-.103 ie=-.524 flex=0
15  ml=-5 ap=-5 pd=31.3087 vv=-.058 ie=-.524 flex=0
16  ml=5 ap=0 pd=29.0356 vv=.052 ie=0 flex=0
17  ml=5 ap=10 pd=31.8823 vv=.041 ie=0 flex=0
18  ml=5 ap=5 pd=30.5539 vv=.062 ie=0 flex=0
19  ml=5 ap=-10 pd=30.5539 vv=.057 ie=0 flex=0
20  ml=5 ap=-5 pd=29.6051 vv=.049 ie=0 flex=0
21  ml=0 ap=0 pd=27.1378 vv=0 ie=0 flex=0
22  ml=0 ap=10 pd=31.5026 vv=0 ie=0 flex=0
23  ml=0 ap=5 pd=29.7946 vv=0 ie=0 flex=0
24  ml=0 ap=-10 pd=30.364 vv=0 ie=0 flex=0
25  ml=0 ap=-5 pd=28.656 vv=0 ie=0 flex=0
26  ml=-5 ap=0 pd=29.4663 vv=-.039 ie=0 flex=0
27  ml=-5 ap=10 pd=31.6925 vv=-.046 ie=0 flex=0
28  ml=-5 ap=5 pd=30.1743 vv=-.057 ie=0 flex=0
```

METHOD FOR DETERMINING CONTACT POSITION PARAMETERS OF A JOINT CONNECTING TWO BONES

RELATED APPLICATION DATA

This application is a national phase application of International Application No. PCT/EP2011/072323 filed Dec. 9, 2011 and published in the English language.

The present invention relates to a data processing method for determining six parameters of a contact position of a joint which connects two bones, a computer program implementing said method and a computer executing said computer program.

In the human anatomy, two bones are typically connected via a joint which exhibits certain kinematic properties. The kinematic properties define a range of motion between the two bones. In other words, the joint typically supports a range of relative positions between the two bones. Such a relative position usually is a contact position in which the surfaces of the two bones are in contact with each other. In particular, there are two or three points of contact or a line contact between the two bones. In general, each contact position is defined by six parameters, wherein three parameters define a translational shift in three dimensions which are typically pairwise orthogonal. In a preferred example, the directions of the shifts are the proximodistal (pd) direction, the anterioposterior (ap) direction and the mediolateral (ml) direction. The other three parameters define a rotational shift or angular alignment, preferably about three pairwise orthogonal axes. Preferably, the three rotational parameters relate to the flexion/extension angle (fe), the internal/external angle (ie) and the varus/valgus angle (vv). In particular, the six parameters of a contact position describe the relative position between a first coordinate system of the first bone and a second coordinate system of the second bone.

The inventor has found that there are certain desired applications which require the six parameters of a contact position when a subset of the parameters of the contact position is given. An exemplary application is the visualization of the range of motion of the joint. The inventor has thus discovered the need to provide a method for determining the six parameters of a contact position of a joint which connects two bones, wherein the method in particular should be computationally effective in order to allow a real-time or on-the-fly determination.

The present invention thus relates to a data processing method for determining six parameters of a contact position of a joint which connects two bones. One step of the method is acquiring a plurality of sample contact position datasets, wherein each dataset comprises six parameters. These six parameters of the sample contact position datasets correspond to the six parameters describing the contact position. The sample contact position datasets, also referred to as node datasets, represent known contact positions of the two bones via the joint.

The method further comprises the step of acquiring a subset of n of the parameters of the contact position as an input parameter dataset. In other words, n of the parameters of the contact position are predetermined, while the remaining parameters of the contact position have to be determined. The variable n is an integer in the range of 1 to 5, preferably in the range of 3 to 5, and more preferably n has the value of 4.

Other steps of the method are selecting at least two of the sample contact position datasets or of a subset of the sample contact position datasets based on the input parameter dataset and determining the m=6−n remaining parameters of the contact position based on the at least two selected sample contact position datasets. In other words, the input parameter dataset is used to select two or more appropriate sample contact position datasets from which the remaining parameters of the contact position are calculated.

With this approach, a database of sample contact position datasets representing discrete sample contact positions of the joint is used as a basis for calculating the six parameters of any (intermediate) contact position. Since the method according to the present invention does not use a computationally extensive model, such as a collision detection model, to determine the remaining parameters, but approximates the remaining parameters from (surrounding) sample contact positions, the determination is considerably fast.

Preferably, the remaining parameters are determined by interpolation or extrapolation. In particular, interpolation is preferably applied if all n parameters of the input parameter dataset are lying between the corresponding n parameters of the selected sample contact position datasets. Extrapolation is preferably applied if at least one of the n parameters of the input parameter dataset is lying beyond the corresponding parameters of the selected sample contact position datasets.

The selected sample contact position datasets must be suitable for determining the remaining parameters of the contact position. Preferably, the selected sample contact position datasets correspond to sample contact positions which are, regarding the n input parameters, the nearest neighbors of the contact position. In other words, the criterion for selecting a sample contact position dataset is the distance between the n parameters of the input parameter dataset and the corresponding parameters of a sample contact position dataset. Nearest neighbors of the contact position thus are sample contact positions with a minimum distance to the contact position, wherein the distance is defined by the n input parameters and the corresponding parameters of a sample contact position.

A maximum distance between the input parameters of the contact position and the corresponding parameters of the sample contact positions can be defined, wherein sample contact positions with a larger distance cannot be selected. Further, a minimum number of sample contact positions to be selected can be defined. Other approaches for selecting sample contact position datasets may be applied. For example, the dimensions in which the distance between the input parameters and the corresponding parameters of the contact position is calculated can be weighted.

As another option, some sample contact position datasets are excluded from being selected. In one example, if the sample contact positions are equally spaced, or are at least arranged in a regular grid, and the value of an input parameter equals one of the discrete values of the corresponding parameter, then only sample contact positions having this particular value are selected, even if the distance of a sample contact position with another value of this parameter has a smaller distance. This can for example be achieved by weighting the parameters appropriately when the distance is calculated.

In one embodiment, the distance between the contact position and a sample contact position is calculated using a Minkowski distance function. For n parameters, the p-norm distance is therefore given by the expression $$\left(\sum_{i=1}^{n}|x_i - y_i|^p\right)^{1/p}$$

with $p \geq 1$. The variable x represents the contact position, the variable y represents a sample contact position and i is an index for the input parameters.

In general, any suitable approach can be used for the interpolation or the extrapolation. However, preferred types of interpolation are a spline interpolation or an interpolation using inverse distance weighting. Spline interpolation in particular refers to a third degree spline interpolation, but also encompasses any other grades as well as B-splines or Bezier curves.

Inverse distance weighting is simple in implementation and can easily be applied to irregularly distributed data. An example for inverse distance weighting is given by the formula $$u(x) = \sum_{i=0}^{S} \frac{w_i(x) u_i}{\sum_{j=0}^{S} w_j(x)}$$

with $$w_i(x) = \frac{1}{d(x, x_i)^p}$$

In this formula, u is the parameter value to be determined at the contact position x. It is calculated based on S neighbors. The values of the corresponding parameter in the selected S neighbors are given by $u_i$ with i running from 1 to S. The variable d describes the distance, regarding the n input parameters, between a neighbor $x_i$ and the contact position x. The variable w is a weighting factor or weight which depends on the distance d. The parameter p is a positive real number shaping the interpolation characteristics.

In one embodiment, the sample contact position datasets are arranged in an n-dimensional array and each array entry comprises the m remaining parameters. With this organizational data structure, the selection of the at least two sample contact position datasets is easy and computationally effective, in particular if the sample contact positions are arranged at equidistant intervals. This means that the values of one particular parameter of the sample contact position, and in particular of all n parameters of the sample contact position which are used as input parameters, can assume discrete values, wherein the discrete values have an equidistant distance.

With sample contact positions at equidistant intervals, the selection of two or more sample contact position datasets is computationally effective, in particular if the index in a dimension of the array corresponds to a multiple of the equidistant interval. If, for example, the interval for an angle is 5 degrees, then an index of 0 corresponds to 0 degrees, an index of 1 corresponds to 5 degrees, an index of 2 corresponds to 10 degrees, and so on. As an option, an offset is added to the index in order to represent shifts symmetrically arranged around a zero shift. So if an angle as one parameter of the contact position is given in 5 degree increments and the index i in the corresponding dimension of the array runs from 0 to 71, then the angle corresponding to an index i is given by i×5 degrees—175 degrees. In a reverse manner, the array index of a sample contact position can be calculated from an angle.

In another embodiment, the sample contact position datasets are stored as lists of six parameters each. For example, the six parameters are consecutively written in a line of a text and each line of the text constitutes a sample contact position dataset. With this approach, the parameters of the contact position which form the input parameters can easily be adapted to the desired application in which the method according to the present invention is used. For example, in one application the remaining parameters are two angles, such as flexion/extension and varus/valgus, while in another application the remaining parameters are all translational shift parameters. Of course, any combination of translational and rotational parameters can constitute the remaining parameters.

In one embodiment, a sample contact position dataset is void for an impossible joint contact position. An impossible joint contact position is a contact position which cannot be assumed by the joint. For example, a sample contact position dataset can be made void by assigning a particular value to one of the parameters. In one exemplary implementation, a value outside of the possible range of 360 degrees is assigned to a parameter corresponding to an angle. Since an angle can only lie within a 360 degree range, a value outside this range can be used to indicate a void dataset.

In another embodiment, a sample contact position dataset further comprises affiliate information, also referred to as label, which indicates that the sample contact position belongs to a contact profile of contact positions. A contact profile of contact positions represents for example a particular movement, such as for walking or standing up regarding a knee joint. A contact profile consists of a sequence of contact positions. Preferably, an additional parameter further defines the position of the sample contact position within the sequence of contact positions, i.e. the sequence number.

The labels enable filtering of the sample contact position datasets. In one embodiment, neighbors for interpolating or extrapolating are only selected from sample contact position datasets which have a predetermined label, in particular a label corresponding to a contact profile. Sample contact positions with a particular label may be used as nodes for finer subdivision of the path between them.

Affiliate information can further comprise a 4×4 matrix which describes the spatial transformation from one bone, or implant, to the other(s).

In another embodiment, the step of determining the m=6−n remaining parameters of the contact position is repeated for a sequence of input parameter datasets, which is also referred to as a parameter profile, thus resulting in a sequence of contact positions. The parameter profile preferably represents a particular movement. With this embodiment, the properties of the joint can be determined for a particular sequence of input parameters for analysis. For example, the properties of the joint can be displayed graphically, for example by plotting the remaining parameters as curves over the variation of the input parameters. In addition, the bones connected by the joint can be displayed in an animation representing the sequence of input parameter datasets.

One aspect of the present invention relates to the acquisition of a sample contact position dataset. In one embodiment, a sample contact position dataset is determined by virtually positioning three-dimensional images of the two bones in a computer such that they are in contact. This might be done using a CAD software provided with a 3D representation of the bones or at least the parts of the bones which form the joint. In the software, the relative position of the two bones is modified until they are in contact. This relative position of the bones thus positioned is then used as a sample contact position. In a particular embodiment, the relative position between the two bones is adjusted manually, for example using an input device such as a mouse, a joystick, a trackball, a pointer or a touch screen. The capabilities of the CAD software can be used in order to determine whether or not the two bones are in contact. The software can for example display a cross-sectional view or a perspective which could not be assumed in the real world, for example from within one of the bones or a cavity of one of the bones.

As an option, a sample position dataset is automatically determined by using collision detection of three-dimensional models of the two bones.

As an alternative, a sample contact position dataset is determined by measuring a real joint. A real joint is physiological joint, for example formed by the two bones or two components of an implant which form an artificial point.

The method in accordance with the invention is a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

Preferably, the inventive method is at least partly executed by a computer. That is, all steps or just some of the steps (i.e. less than a total number of steps) of the inventive method may be executed by a computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

It lies within the scope of the present invention to combine one or more features of two or more embodiments, implementations or examples as long as technically feasible. It shall be noted that a joint connecting the two bones can be an artificial joint or a natural (non-artificial or physiological) joint. In an artificial joint, two components, or implants, replace parts of the two bones. The joint can in particular be a knee joint, but is not limited to this.

The invention shall be explained in more detail with reference to the accompanying figures. The figures show.

Figure 1A:
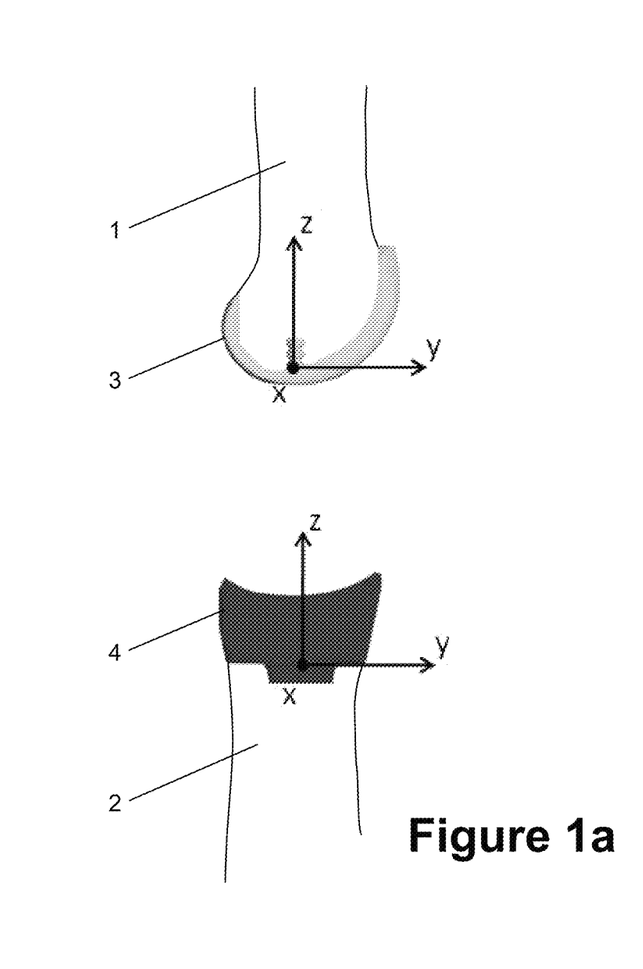
FIG. 1a two components of an artificial knee joint in a side view.

FIG. 1a schematically shows a side sectional view of a femur 1 as first bone and a tibia 2 as a second bone. A femur implant 3 is attached to the femur 1 and a tibia implant 4 is attached to the tibia 2. The femur implant 3 and the tibia implant 4 constitute an artificial knee joint. As can be seen from FIG. 1a, a coordinate system is defined for each implant, and thus for each bone. It is to be noted that attaching an implant to a bone is not a part of the present invention which only relates to the analysis of a joint.

Figure 1B:
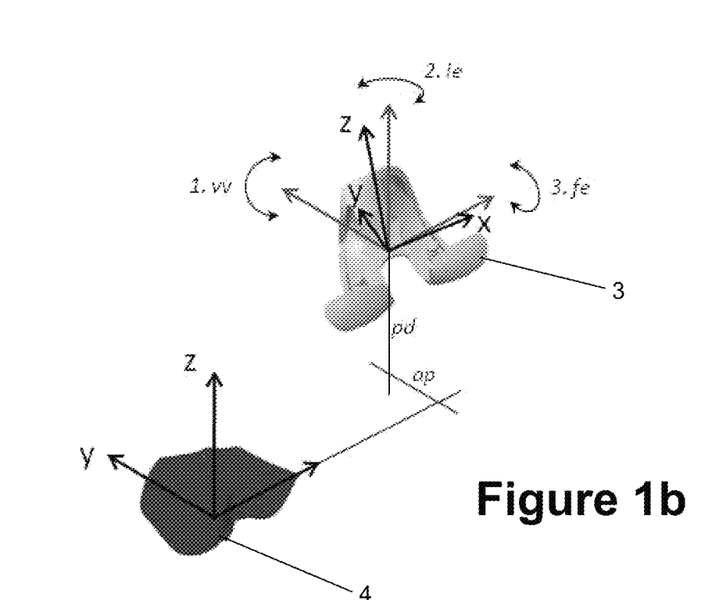
FIG. 1b the components of FIG. 1A in a perspective view.

FIG. 1b shows a perspective view of the implants 3 and 4. Next to the coordinate systems attached to the implants, the six parameters which define the relative position between the coordinate systems, and therefore between the implants 3 and 4, are indicated. Three of the six parameters represent translational shifts in the proximodistal (pd), anteriorposterior (ap) and mediolateral (ml) directions. The other three of the six parameters correspond to rotations about certain axes representing a flexion/extension (fe or flex) angle, an internal/external (ie) angle and a varus/valgus (vv) angle, respectively. Preferably, the coordinate systems associated with the implants are arranged such that the six parameters represent meaningful medical terms. A contact position is a relative position between the coordinate systems of the implants such that the bones (or implants) are in contact.

Figure 8:
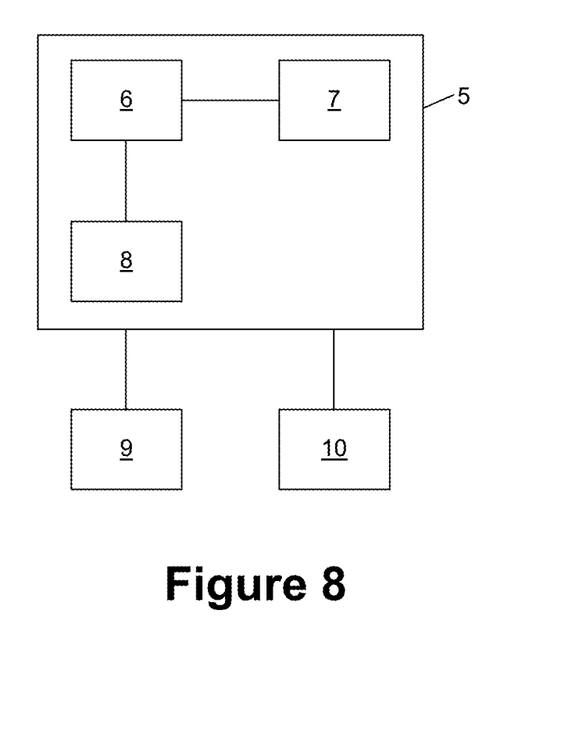
FIG. 8 a schematic structure of an apparatus for carrying out the method.

FIG. 8 shows a computer 5 for carrying out the method according to the present invention. The computer 5 comprises a central processing unit 6 connected to a memory 7 and an interface 8. Connected to the computer 5 is an input device 9 and a display device 10. In the present example, the input device 9 is a mouse or a keyboard. The memory 7 stores data and provides the data to the central processing unit 6. Additional data can be acquired or data can be provided by the interface 8.

Figure 2A:
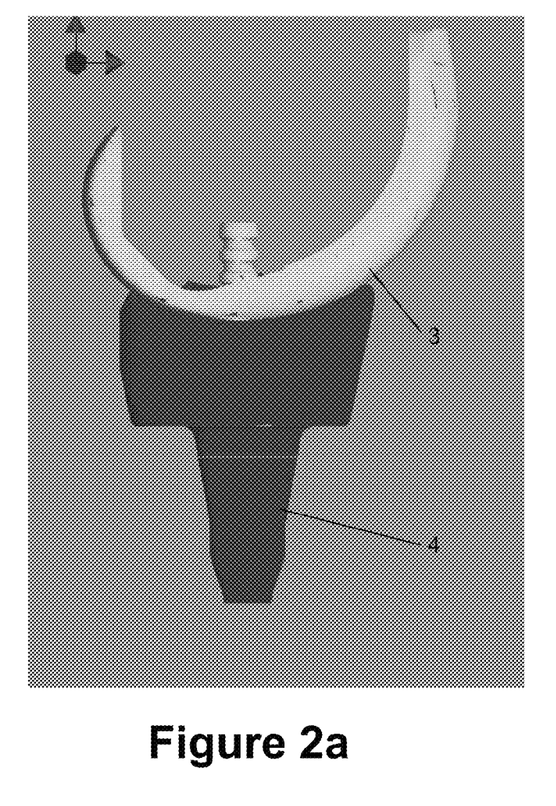
FIG. 2a a first sample contact position.
Figure 2B:
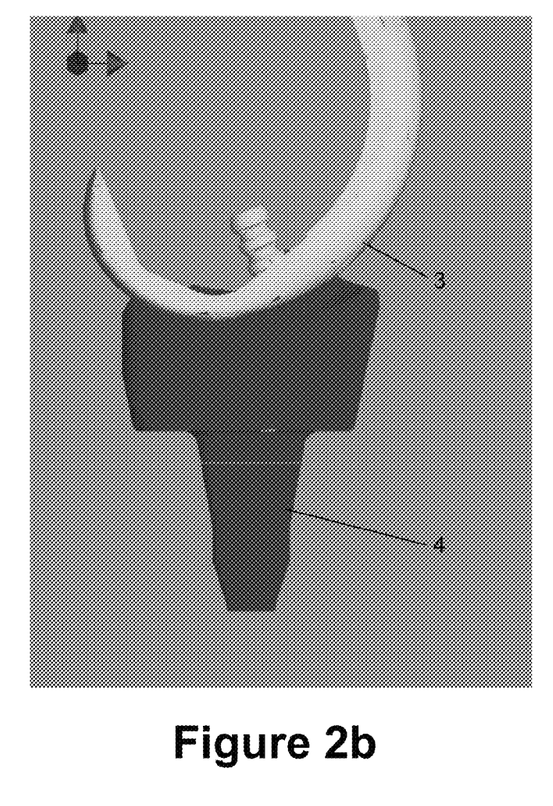
FIG. 2b a second sample contact position.

In a first step of the method, a plurality of sample contact position datasets is acquired. The memory 7 stores 3D-models of the femur implant 3 and the tibia implant 4. For this purpose, a CAD software is running on the central processing unit 6. With the input device 9, the relative position between the models of the implants is adjusted in the computer 5 until the two implants 3 and 4 are in contact at at least two contact points. Such a relative position is called a contact position of the joint. FIG. 2a shows first such contact position, while FIG. 2b shows second such contact position.

Figure 3:
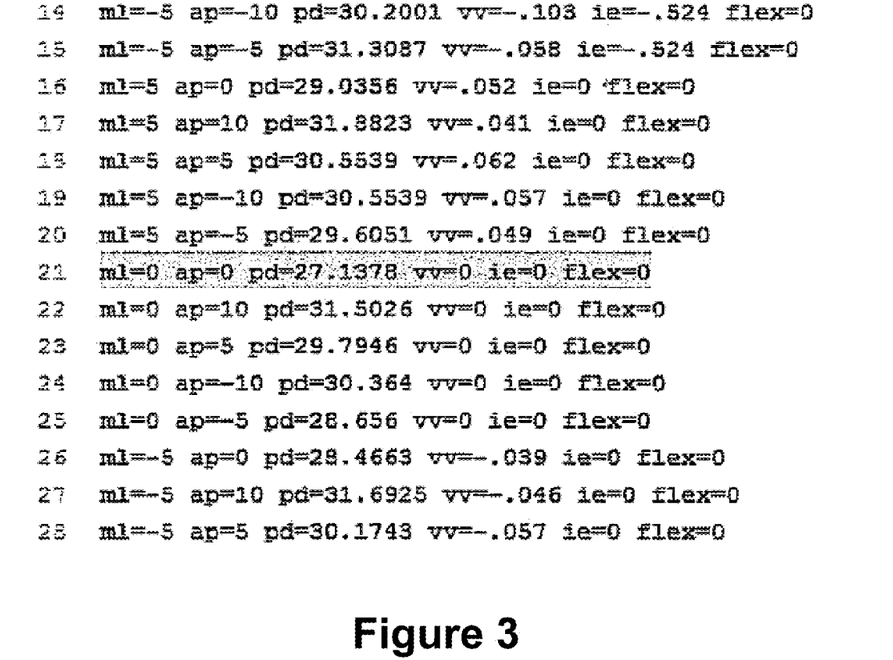
FIG. 3 a list of sample contact position datasets.

Only a reasonable number of different sample contact positions may be established and stored in order to limit efforts. The sample contact positions represent an extract of the infinite number of all possible contact positions in a continuous parameter space. In this exemplary embodiment, the sample contact positions are stored in a list of sample contact positions as shown in FIG. 3. Each line of the list contains a sample contact position dataset representing the six parameters of a sample contact position. The parameters in line 21 correspond to the sample contact position shown in FIG. 2a.

In a plurality of applications, it is advantageous to know the contact position of the joint under certain conditions, such as for a predetermined subset of some of the parameters of the contact position. However, it is elaborately or computationally complex to determine the remaining parameters from the 3D models, in particular if a determination in real time is required. The present invention therefore makes use of sample contact positions, or nodes, which are then appropriately interpolated or extrapolated. This is schematically shown in FIG. 4.

Figure 4:
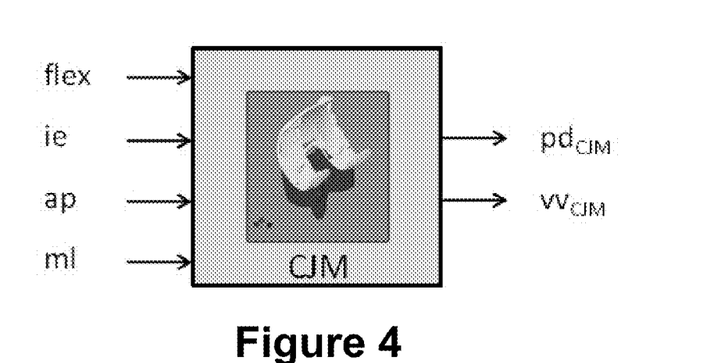
FIG. 4 a schematic representation of the method.

According to FIG. 4, a block which represents the method according to the present invention is shown. This block is also called a continuous joint model (CJM). A subset of four of the parameters of the contact position is provided to the model as input parameters represented by an input parameter dataset. In the present example, those parameters are fe, ie, ap and ml. The continuous joint model then calculates the remaining parameters pd and vv based on the input parameter datasets and the sample contact position datasets. An index CJM of the parameters pd and vv indicates that these parameters were calculated using the continuous joint model.

The continuous joint model selects at least two of the sample contact position datasets based on the input parameter dataset. In this exemplary embodiment, the continuous joint model selects the two nearest neighbors of the contact position. The nearest neighbors are those sample contact positions with the smallest distance to the contact position. Since the parameters pd and vv of the contact position are to be determined, this distance is calculated based on the parameters fe, ie, ap and ml only.

As an example, the parameters pd and vv of a contact position with the parameters ml=0, ap=2.5, ie=0 and flex=0 have to be determined. The continuous joint model identifies the sample contact positions in lines 21 and 23 of the list shown in FIG. 3 as the nearest neighbors. The values for the parameters pd and vv are then calculated by interpolating the corresponding parameter values in the selected sample contact positions. This results in the values of vv=0 and pd=28.4662.

Figure 5:
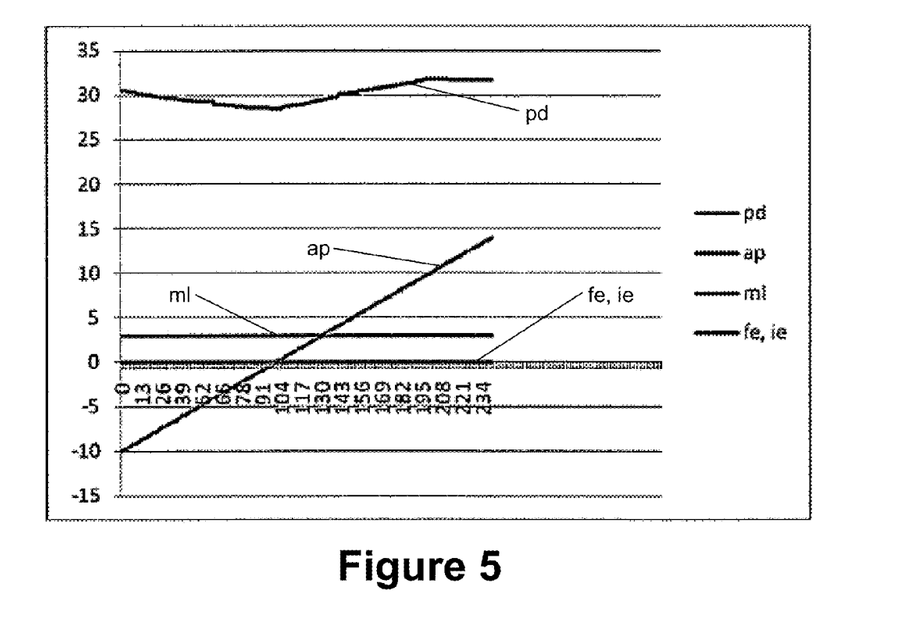
FIG. 5 a graph showing an output of the method.

With the present invention, the kinematical properties of a joint can easily be determined. This is achieved by providing a sequence of input parameter datasets and calculating the corresponding sequence of contact positions. FIG. 5 shows a graph representing the result of the determination based on a sequence of input parameter datasets. For this example, the input parameters fe and ie are fixed to 0 degrees and ml is fixed to 3 mm across the whole sequence and ap is varied linearly from −10 mm to +13 mm. The parameter pd is calculated by the continuous joint model and follows the graph shown in FIG. 5. The parameter vv is also calculated by the continuous joint model, but not shown in the figure. From the graph of pd, it can be seen that the femur implant 3 sinks into the cavity of the tibia implant 4 and ascents again when shifted further to anterior.

Figure 6:
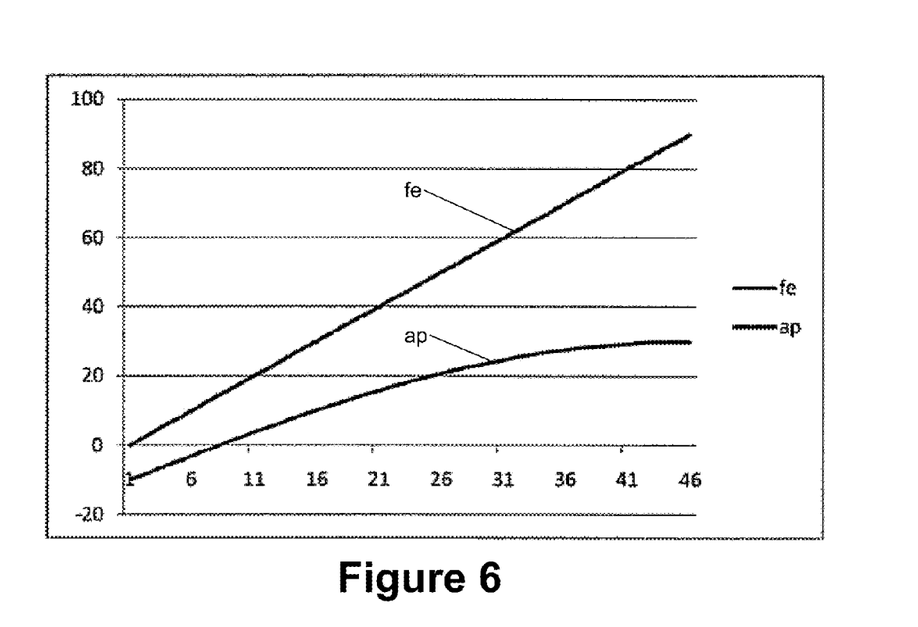
FIG. 6 a graph showing two input parameters.
Figure 7A:
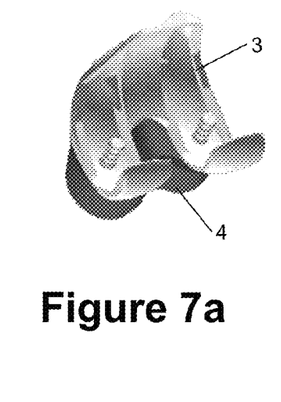
FIG. 7 a sequence of contact positions.
Figure 7B:
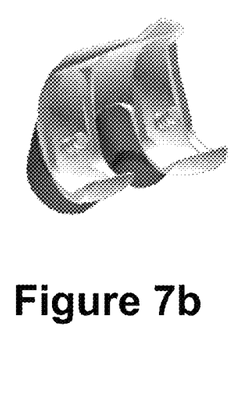
Figure 7C:
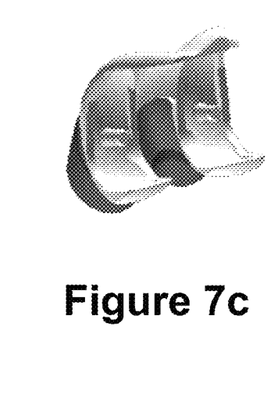
Figure 7D:
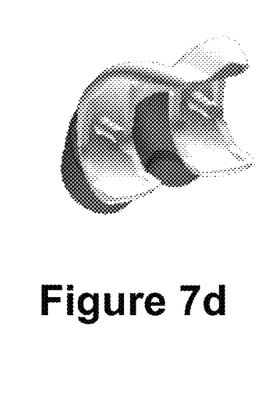
Figure 7E:
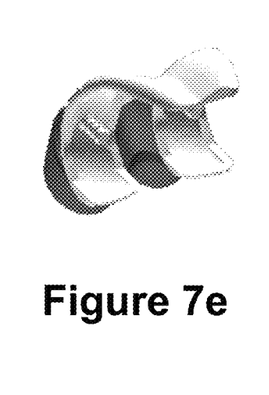

The sequence of input parameter datasets preferably represents a parameter profile for a sequence of contact positions. The parameter profile in particular describes a certain movement. The graphs shown in FIG. 6 represent the parameters fe and ap for the bending movement of the knee joint. The value of the parameter fe increases linearly from 0 degrees to 90 degrees, while ap represents the relative anterior-posterior shift of the implants 3 and 4 during the bending movement. The parameter ml was set to 0 mm, while the parameter ie was set to 0 degrees for the whole sequence. A continuous joint model was then used to calculate the remaining parameters vv and pd.

The thus calculated sequence of contact positions can be used to visualize the kinematical behavior of the knee joint. FIGS. 7a to 7e show five exemplary contact positions out of this sequence. The sequence of contact positions can also be animated to show the kinematical properties.

The invention claimed is:

1. A data processing method performed in a computer having a memory for determining six parameters of a contact position of a physiological or artificial joint which connects two bones, wherein the contact position is a relative position between the two bones in which physiological or artificial surfaces defined at ends of the two bones respectively by the bones or by implants carried on the bones are in contact with each other, and wherein three of the parameters define a translational shift and three of the parameters define a rotational shift, the method comprising:
   acquiring a plurality of sample contact position datasets, each dataset comprising six parameters that correspond to the six parameters describing the contact position;
   acquiring a subset of n of the parameters of the contact position as an input parameter dataset;
   selecting at least two of the sample contact position datasets based on the input parameter dataset; and
   determining the m=6−n remaining parameters of the contact position based on the at least two selected sample contact position datasets.

2. The method of claim 1, wherein the remaining parameters are determined by interpolation or extrapolation.

3. The method according to claim 2, wherein the interpolation is a spline interpolation or uses inverse distance weighting.

4. The method according to claim 1, wherein the selected sample contact position datasets correspond to sample contact positions which are, regarding the input parameters, the nearest neighbors of the contact position.

5. The method of claim 4, wherein a distance between the contact position and a sample contact position is calculated using a Minkowski distance function.

6. The method according to claim 1, wherein the sample contact position datasets are arranged in an n-dimensional array and each array entry comprises the m remaining parameters.

7. The method according to claim 1, wherein the sample contact positions are arranged at equidistant intervals.

8. The method according to claim 1, wherein a sample contact position dataset is void for an impossible joint contact position.

9. The method of claim 1, wherein a sample contact position dataset further comprises affiliate information which indicates that the sample contact position belongs to a contact profile of contact positions.

10. The method according to claim 1, wherein the step of determining the m=6−n remaining parameters of the contact position is repeated for a sequence of input parameter datasets, thus resulting in a sequence of contact positions.

11. The method according to claim 1, wherein a sample position dataset is determined by virtually positioning three-dimensional images of the two bones such that they are in contact and using the relative position of the bones thus positioned as a sample contact position.

12. The method according to claim 1, wherein a sample position dataset is automatically determined by using collision detection of three-dimensional models of the two bones.

13. The method according to claim 1, wherein a sample position dataset is determined by measuring a real joint.

14. A computer program embodied on a non-transitory computer readable medium which, when running on a computer or when loaded onto a computer, causes the computer to determine six parameters of a contact position of a physiological or artificial joint which connects two bones, wherein the contact position is a relative position between the two bones in which physiological or artificial surfaces defined at ends of the two bones respectively by the bones or by implants carried on the bones are in contact with each other, and wherein three of the parameters define a translational shift and three of the parameters define a rotational shift, by performing steps comprising:
   acquiring a plurality of sample contact position datasets, each dataset comprising six parameters that correspond to the six parameters describing the contact position;
   acquiring a subset of n of the parameters of the contact position as an input parameter dataset;
   selecting at least two of the sample contact position datasets based on the input parameter dataset; and
   determining the m=6−n remaining parameters of the contact position based on the at least two selected sample contact position datasets.

15. A computer on which the computer program according to claim 14 is running or into the memory of which the computer program is loaded.

* * * * *

UNITED STATES PATENT AND TRADEMARK OFFICE
CERTIFICATE OF CORRECTION

PATENT NO. : 9,852,268 B2  
APPLICATION NO. : 14/363040  
DATED : December 26, 2017  
INVENTOR(S) : Hubert Goette Page 1 of 1

It is certified that error appears in the above-identified patent and that said Letters Patent is hereby corrected as shown below:

On the Title Page

Item (75) should read:  
Inventor: Hubert Goette, Munich (DE)

Signed and Sealed this  
First Day of May, 2018

Andrei Iancu  
*Director of the United States Patent and Trademark Office*